United States Patent
Weckstrom

(10) Patent No.: US 8,286,504 B2
(45) Date of Patent: Oct. 16, 2012

(54) ARRANGEMENT FOR IMPROVING ACCURACY OF PRESSURE MEASUREMENT AND FLOW SENSOR

(75) Inventor: Kurt Weckstrom, Espoo (FI)

(73) Assignee: General Electric Company, Schenectady, NY (US)

(*) Notice: Subject to any disclaimer, the term of this patent is extended or adjusted under 35 U.S.C. 154(b) by 295 days.

(21) Appl. No.: 12/720,754

(22) Filed: Mar. 10, 2010

(65) Prior Publication Data

US 2010/0242622 A1    Sep. 30, 2010

(30) Foreign Application Priority Data

Mar. 27, 2009   (EP) .................................... 09396003

(51) Int. Cl.
*G01F 1/37*   (2006.01)
(52) U.S. Cl. .................................... 73/861.52
(58) Field of Classification Search ............... 73/861.52, 73/861.51, 861.63; 128/204.23; 604/283
See application file for complete search history.

(56) References Cited

U.S. PATENT DOCUMENTS

| | | | | |
|---|---|---|---|---|
| 3,089,331 A | * | 5/1963 | Sharko et al. ................... | 73/1.58 |
| 3,557,869 A | * | 1/1971 | Weimann et al. .............. | 165/111 |
| 4,599,906 A | * | 7/1986 | Freud et al. ................ | 73/861.47 |
| 5,088,332 A | | 2/1992 | Merilainen et al. | |
| 5,287,851 A | | 2/1994 | Beran et al. | |
| 5,913,249 A | | 6/1999 | Weckstrom | |
| 6,089,105 A | * | 7/2000 | Ricciardelli ............... | 73/861.52 |
| 6,142,148 A | | 11/2000 | Weckstrom et al. | |
| 6,782,746 B1 | * | 8/2004 | Hasselbrink et al. .......... | 73/253 |
| 7,032,463 B2 | | 4/2006 | Misholi et al. | |
| 2006/0117856 A1 | | 6/2006 | Orr et al. | |

FOREIGN PATENT DOCUMENTS

| | | |
|---|---|---|
| DE | 4034176 A1 | 11/1991 |
| EP | 0815792 A | 1/1998 |
| EP | 1782731 A | 5/2007 |
| EP | 1820528 A | 8/2007 |
| WO | 9841148 A | 9/1998 |
| WO | 2004039444 A | 5/2004 |

OTHER PUBLICATIONS

EP Search Report issued on Apr. 8, 2009 to EP Patent Application No. 09396003.7.

* cited by examiner

*Primary Examiner* — Jewel V Thompson
(74) *Attorney, Agent, or Firm* — Global Patent Operation

(57) ABSTRACT

An arrangement for improving an accuracy of a pressure measurement made of a breathing gas including drops of water or humidity flowing along a flow channel is disclosed herein. The arrangement includes at least one pressure measuring channel to transmit a pressure of the breathing gas flowing along the flow channel to a measuring device to make the pressure measurement. The pressure measuring channel is equipped with a capillary material enabling capillary suctioning of water. Also a flow sensor for a flow rate measurement of a breathing gas including drops of water or humidity is provided.

20 Claims, 2 Drawing Sheets

ARRANGEMENT FOR IMPROVING ACCURACY OF PRESSURE MEASUREMENT AND FLOW SENSOR

CROSS-REFERENCE TO RELATED APPLICATIONS

This application claims priority under 35 U.S.C. §§119(a)-(d) or (f) to prior-filed, co-pending European patent application number 09396003.7, filed on Mar. 27, 2009, which is hereby incorporated by reference in its entirety.

BACKGROUND OF THE INVENTION

This disclosure relates generally to an arrangement for improving an accuracy of a pressure measurement made of a breathing gas including drops of water or humidity flowing along a flow channel. Also this disclosure relates to a flow sensor for a flow rate measurement of a breathing gas including drops of water or humidity.

In hospitals, during intensive care and operations, a respiratory apparatus must mostly be used to take care of a patient's respiration. An unhindered flow of gases into and out of the patient's lungs is naturally of vital importance. A condition of gas channels can be monitored both by measuring concentrations of inhaled and exhaled gases and by measuring a flow and pressure of the gases. Especially, monitoring of the carbon dioxide content of an exhalation gas is widely used as a routine in operating theaters and now more frequently also in the intensive care unit. However, the flow and pressure measurements are an essential additional function both in respect of safety and because they make it possible to calculate quantities descriptive of the mechanical operation and respiratory metabolism of the lungs.

In principle, there are many applicable types of flow sensors. However, measurements under clinical conditions involve many problems. The flow is measured from the end of a so-called intubation tube inserted into the patient's windpipe. The sensor is therefore exposed to humidity, condensed water, and mucous secretions coming from the windpipe. It is clear that such soiling is likely to affect the operation of most types of flow sensors. The main types of flow detector and their principles are presented e.g. in the publication Doebelin: Measurement Systems, McGraw-Hill Kogakusha, 1976. Flow sensors based on differential pressure are best suited for clinical use. The flow in the respiratory tube may be laminar or turbulent. In the case of laminar flow, the pressure difference across a flow restricting element placed in the tube is directly proportional to the flow. In the case of a turbulent flow, the pressure difference depends on the square of the flow. In practice, the relation between the measured pressure difference and the flow always has to be empirically determined for a specific mechanical sensor construction. The flow sensors currently used are generally made of plastic and can either be disposable or reusable. Water condenses as droplets on the interior walls of the sensor and this reduces the cross-sectional area of the flow sensor with subsequent increase in the measured pressure difference and then also the flow signal. This problem with a drifting signal can be severe especially when using the flow sensor under very humid conditions typically for several hours.

One way to eliminate the drift is to heat the sensor to a temperature sufficient to prevent condensation. However, this method requires a heating element and electrical connectors. Another way of dealing with the problem is to treat the inner surface of the sensor in order to reduce the contact angle of the droplets so that they flow out and wet the surface of the sensor evenly. According to another similar method the inner surface is treated with a material retaining water inside it. Any of those methods takes care of the drift in the flow signal. However, there is also a problem with the pressure measuring tubes connecting the differential pressure orifices in the flow path with the differential pressure sensor. Small amounts of water can enter these narrow tubes even if there is no net flow in the tubes, only a minor to-and-fro fluctuation as a consequence of pressure changes in the respiratory tube. If the water clogs either one of those tubes there will be a fast change in the pressure difference to a new level, which is incorrect. Most frequently, the water enters the orifice closest to the patient because of the more humid exhaled gas. Condensed water droplets also often detach from the walls in the respiratory tube when the patient is turned or moved and may as a consequence flow into the orifices.

One remedy is to heat the orifices and tube entrances, but this method is not customer friendly as mentioned above. Another method is to design the sensor adapter in such a way that water is unlikely to enter the orifices. This may work in many cases, but under very wet conditions like prolonged use in critical care, water may still enter the pressure measuring tubes and cause erroneous signal levels. One method would be to cover the orifices with a hydrophobic porous membrane. Even if no water then can enter the pressure measuring tubes the membrane will cause a pressure drop which may not be constant under very wet conditions or when the membrane gets soiled with mucus. This would induce an error in the measured flow value. Still another method uses a minimal purge flow in the measuring tubes away from the pressure sensors. This method mostly works but it is technically a more complicated and also expensive construction. Further, it could contaminate the respiratory tube.

BRIEF DESCRIPTION OF THE INVENTION

The above-mentioned shortcomings, disadvantages and problems are addressed herein which will be understood by reading and understanding the following specification.

In an embodiment, an arrangement for improving an accuracy of a pressure measurement made of a breathing gas including drops of water or humidity flowing along a flow channel includes at least one pressure measuring channel configured to transmit a pressure of the breathing gas flowing along the flow channel to a measuring device to make the pressure measurement. The pressure measuring channel is equipped with a capillary material enabling capillary suctioning of water.

In another embodiment, an arrangement for improving an accuracy of a pressure measurement made of a flowing breathing gas with drops of water or humidity includes a flow channel along which the breathing gas is flowing and a restricting element in the flow channel for the differential pressure measurement. The arrangement for improving the an accuracy of a pressure measurement made of a flowing breathing gas with drops of water or humidity also includes at least two pressure measuring channels, one of the two pressure measuring channels being connected to one side of the restricting element and another of the two pressure measuring channels being connected to another side of the restricting element, the two pressure measuring channels transmitting pressure signals of the breathing gas on both sides of the restricting element to a measuring device to make the differential pressure measurement. At least one of the pressure measuring channels is equipped with a capillary material enabling capillary suctioning of water.

In yet another embodiment a flow sensor for a flow rate measurement of a breathing gas including drops of water or humidity includes a flow channel along which the breathing gas is flowing and a restricting element in the flow channel for the differential pressure measurement. The flow sensor for a flow rate measurement of a breathing gas including drops of water or humidity also includes at least two pressure measuring channels, one of the two pressure measuring channels being connected to one side of the restricting element and another of the two pressure measuring channels being connected to another side of the restricting element, the two pressure measuring channels transmitting pressure signals of the breathing gas on both sides of the restricting element to a measuring device to make the flow rate measurement. At least one of the pressure measuring channels is equipped with a capillary material enabling capillary suctioning of water for improving an accuracy of the flow rate measurement.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
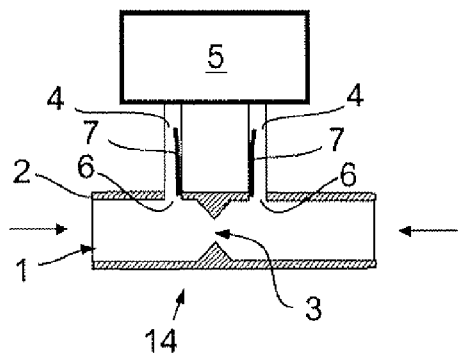
FIG. 1 is a general cross sectional side view of an arrangement for pressure measurement in accordance with an embodiment.
Figure 2:
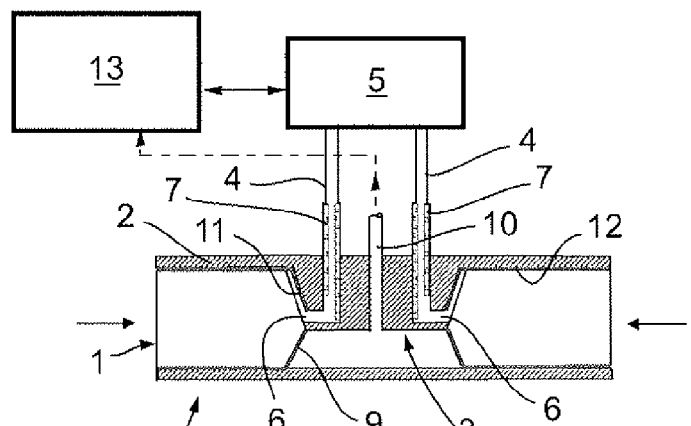
FIG. 2 is a general cross sectional side view of an arrangement for pressure measurement in accordance with a second embodiment.

FIGS. 1 and 2 present different types of arrangements for improving an accuracy of a pressure measurement, especially a breathing gas pressure measurement, either can be measured an absolute pressure or a differential pressure. The differential pressure of a gas flow can be measured over a flow restriction indicating a flow rate. The arrangement for measuring the differential pressure can include a separate flow sensor or the flow sensor is an integral part of a channel conveying a breathing gas. The flow sensors can also be used to measure the absolute pressure, in which case the breathing gas pressure is compared to outside pressure.

Figure 4:
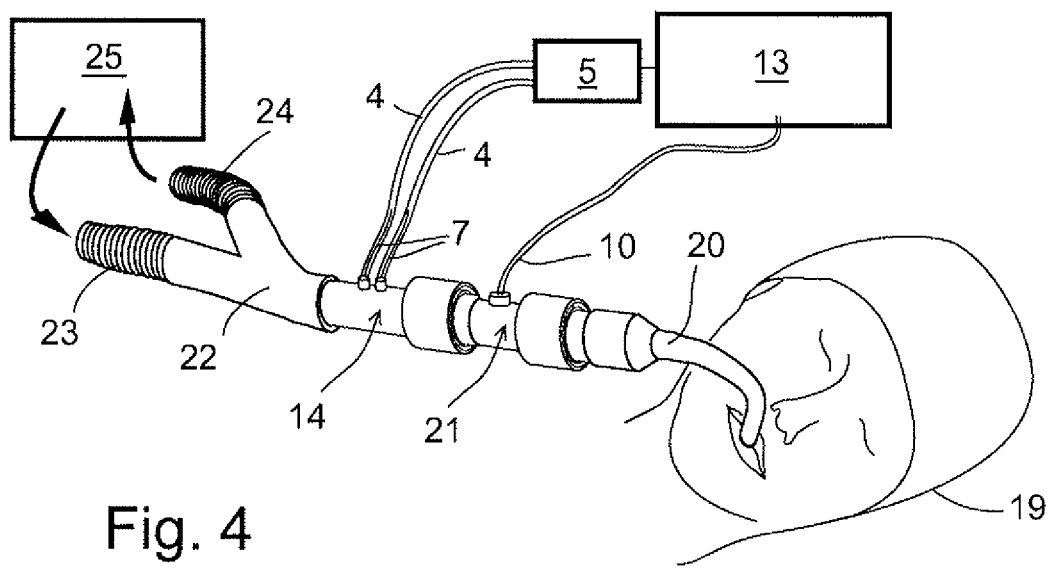
FIG. 4 is a perspective view of an arrangement for a pressure measurement shown in FIG. 1 in an operating environment.

The flow sensors 14 presented in FIGS. 1 and 2 comprise a flow channel 1 for conveying a gas flow to be measured. The flow channel 1, which may be tubular, is delimited by a wall 2 and it is provided with a flow restricting element 3 to restrict gas flow in flow channel 1. For the pressure measurement at least one pressure measuring channel 4 is needed to communicate with the flow channel 1 transmitting the pressure of the breathing gas flowing along the flow channel 1 to the measuring device 5. For the differential pressure measurement two pressure measuring channels 4 are necessary. Another end of the at least one pressure measuring channel 4 is connected to a measuring device 5, which can be for the measurement of the pressure or the pressure difference created in the flow channel 1 by the action of the flow restricting element 3. The pressure measuring channels 4 for connecting the flow sensor 14 to the measuring device 5 often comprise flexible tubing, either integral with the flow sensor or as detachable tubing suitable for the purpose as shown in FIG. 4 but the measuring device 5 can also be connected directly to the flow sensor 14 with very short pressure measuring channels 4.

A surface of the wall 2 of the flow channel 1 and/or the restricting element 3, which are directly exposed to the gas flow, may have a treatment providing reduced surface tension or water retention but it may also directly be the surface of the material from which the flow channel 1 is constructed, normally a polymer or a metal.

In the embodiment illustrated in FIG. 1, the restricting element 3 restricting the flow in the flow channel 1 has orifices 6 of the pressure measuring channels 4 on both sides of it. These channels are connected to a measuring device 5, which is measuring a pressure difference. The restricting element 3 may have different appearances but the pressure difference is always measured across it. The gas may flow in the flow channel 1 in either direction as indicated by arrows but the humidity load may be heavier in one direction. In respiratory use this is often the direction from a patient to the flow sensor. If this direction is from right to left, then the right pressure measuring channel 4 is more exposed to condensed water and may become obstructed during prolonged use. A contributing factor comes from the fact that the flow sensor normally is tilted down from the patient. If the pressure measuring channel 4 is clogged the pressure level in that channel will be erroneous with the consequence that the pressure difference between the two pressure measuring channels 4 and also the flow value from the measuring device 5 is useless. In order to prevent the obstruction in pressure measuring channel 4 a capillary material 7 such as a capillary element e.g. in the form of a wick may be inserted into the pressure measuring channel and advantageously into its end closest to the flow channel 1. It is advantageous to equip with the capillary material 7 at least the one of the measuring channels 4 first receiving the breathing gas exhaled by the patient.

The capillary material 7 is normally made of cotton in the form of a cord, a ribbon, or a tubular appearance. Any other material with fast capillary suctioning of water, e.g. a wick made of polypropylene, is usable. The capillary material 7 can also be a surface modification of the tube material itself. A porous capillary material with a hole in it could constitute the tube, too. The capillary material 7 should have the ability to rapidly suck the small amount of water possibly entering the pressure measuring channel 4 and spread it along the capillary material in order to prevent clogging of the pressure measuring channel 4. Preferably, this water would be transported along the tube back towards the flow channel 1. The capillary material 7 is preferably more or less hydrophilic and can also be hygroscopic even if that is not a requirement.

This capillary material 7 can extend along the pressure measuring channel 4 from about 10 mm to about 200 mm. It does not normally have to be longer because the water drop always starts clogging the measuring channel at the entrance end and there is normally no net flow in the measuring channels 4, only a minimal pressure dependent fluctuation. Of course, the measuring channel 4 may be equipped with the capillary material along its whole length if this is beneficial from the manufacturing standpoint. The capillary material is either part of the pressure measuring channel 4 or mounted inside it. The capillary material 7 may extend into the flow sensor 14 and it could even be part of the flow sensor 14. The fast capillary suctioning of water is especially beneficial because the water drop will enter suddenly if e.g. the patient is turned or moved and the position of the wet flow sensor changes.

The capillary material 7 can be used in either one of the pressure measuring channels 4 or, preferably, in both pressure measuring channels. A use of the capillary material improves the accuracy of the pressure measurement and may prevent artifacts in the flow readings caused by water droplets clogging one or both of the pressure measuring channels 4. A typical diameter of the pressure measuring channel is about 2.5 nun. A water drop of diameter 3 mm is able to obstruct such a channel for a length of about 3 mm. The capillary material 7 should be able to clear that obstruction in less than 1 minute, or more specifically in less than 30 seconds or even more specifically in less than 10 seconds corresponding to about two breaths. Obviously, the problem is less pronounced with a larger pressure measuring channel diameter but then the increased response time of the pressure measurement impairs the flow readings.

As shown in FIG. 2 the restricting element 3 has its pressure measuring orifices 6 close to the center of the flow channel 1. This construction is based on a variation of the Pitot tube and is described in detail in U.S. Pat. No. 5,088,332. Placed near and around the orifices 6 and acting as a restricting element 3 in the flow channel 1 are vanes 9 provided with a groove 11, this embodiment having three such vanes. The arrangement gathers the Pitot pressure evenly from all directions, and changes in the flow profile have almost no effect on the flow measurement. It is also possible to connect to the flow channel 1 a sampling tube 10 for the measurement of gas concentrations, and such a flow sensor 14 is therefore a combination of a so-called spirometer for measuring the volume of the air inspired or expired by the lungs and a sampling adapter for a gas analyzer 13.

The flow channel 1 may have a surface treatment 12 as shown in FIG. 2 to prevent droplets from building up because of condensation. In that case, a signal drift as a consequence of reduced tube diameter can be avoided. Despite this possible surface treatment 12 a drawback especially with the construction with vanes 9 becomes evident under very wet conditions and prolonged use for example occasionally in the intensive care unit or when using a more or less closed respiratory circuit. Water may enter the orifice 6 via one of the vanes 9. The remedy is to use the capillary material 7 with the fast capillary suctioning of water at the beginning of the pressure measuring channel/s 4 or, in other words, at the end of the pressure measuring channel/s 4, which is closer to the flow channel 1. This capillary material 7 such as a capillary element may either be in the form of a wick as described earlier and shown in FIG. 1 or it may be as shown in FIG. 2 a treatment of the inner walls of the measuring channels 4 that can induce a capillary suctioning of water or it may be a porous material including the pressure measuring channels. It may e.g. be possible to make the surface of the pressure measuring channel 4 porous with open cells or the surface may have fine capillary grooves in the channel material. These grooves are preferably longitudinal to enable a simple tube extrusion. The capillary material may also be added to the inner surface of the pressure measuring channels 4 or the channels or the entrance part of them may even be constructed of this material. Such capillary materials are e.g. different hydrophilic porous products provided by Porex Technologies of Fairburn, Ga. The capillary material 7 may extend into the flow channel 1 or may even be part of the flow channel.

Figure 3:
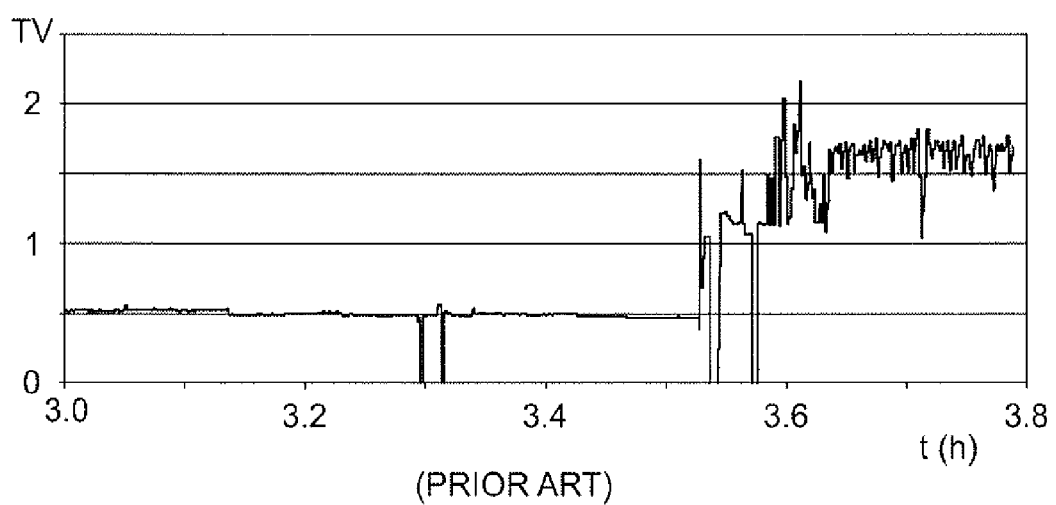
FIG. 3 is a diagram showing a typical problematic pressure measuring result according to prior art.

The problem encountered during a prolonged use under very wet conditions is presented in FIG. 3. A prior art flow sensor was used without a capillary material but the flow sensor had a surface treatment to reduce the surface tension in the flow channel. The curve is a presentation of the expired tidal volume TV in liters as a function of time t in hours. The tidal volume is the volume of air inspired or expired during a respiratory cycle. The measurement is uneventful for more than three hours and the tidal volume is about half a liter. At 3.3 hours a small drop of water enters one of the pressure measuring channels 4 and immediately leaves it again. The differential pressure and, consequently, also the value of the tidal volume is erroneous but resumes to correct value as the clogging water disappears. However, after 3.5 hours the position of the flow sensor is suddenly changed with the consequence that much condensed water is set free. A small part of it enters the orifice 6 and clogs the pressure measuring channel 4. As a result, the differential pressure fluctuates wildly and the value of the tidal volume is completely erroneous. As the situation settles one of the pressure measuring channels is still clogged and the tidal volume shown is more than three times its actual value. In this situation the only remedy is to disconnect the pressure measuring channels and remove the water manually. This operation is time consuming and could even destroy the pressure sensors if e.g. pressurized air is used for the procedure. The use of a capillary material 7 with the fast capillary suctioning of water would have prevented this event and would have allowed several more hours of reliable measuring.

FIG. 4 presents a perspective view of an arrangement for a pressure measurement shown in FIGS. 1 and 2 in an operating environment where an intubation tube 20 is inserted into the windpipe of a patient 19. Connected to a respiratory circuit is a flow sensor 14 as shown in detail in FIG. 1. A connecting piece 21, provided with a sampling tube 10 for the analysis of gas, e.g. measurement of its concentration, is connected between the intubation tube 20 and a Y-shaped piece 22 connecting the inlet and outlet hoses 23, 24 of an apparatus 25 maintaining a respiration. The connecting piece 21 is normally so connected that it lies closest to the patient 19, but it could also be integrated with the flow sensor 14 as in FIG. 2 or it could be placed between the flow sensor 14 and the Y-shaped piece 22. The gas sampling tube 10 is connected to an analyzer 13, in which the gas is measured and the signal is processed so as to produce a display (not shown) showing the variations in the gas concentration under measurement as a function of time, i.e. the respiration curve or concentration readings during inhalation and exhalation. The flow sensor 14 is also connected via a measuring apparatus 5 to the analyzer 13, in which the signal is processed as to produce a display of the flow and pressure readings for inhalation and exhalation and possible other quantities derived from them. The measuring device 5 may also be placed in the analyzer 13 and the gas concentration measurement can be performed in the connecting piece 21 or as integrated with the flow sensor 14, if the device is a so-called mainstream gas sensor.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for improving an accuracy of a pressure measurement made of a breathing gas including drops of water or humidity flowing along a flow channel, comprising:

at least one pressure measuring channel configured to transmit a pressure of the breathing gas flowing along said flow channel to a measuring device to make the pressure measurement;

wherein said pressure measuring channel is equipped with a capillary material enabling capillary suctioning of water.

2. The apparatus according to claim 1, wherein the pressure measurement is an absolute pressure measurement in which case the breathing gas pressure in said channel acquired through said one pressure measuring channel is compared by said measuring device to outside pressure.

3. The apparatus according to claim 1, wherein the pressure measurement is a differential pressure measurement of the breathing gas over a restricting element of said channel to create a pressure difference indicating a flow rate and which pressure difference is transmitted through said at least one pressure measuring channel and another pressure measuring channel from different sides of said restricting element to said measuring device to measure the flow rate.

4. The apparatus according to claim 3, wherein said flow channel and said restricting element are parts of a flow sensor.

5. The apparatus according to claim 3, wherein said flow channel, said restricting element and at least one pressure measuring channel are parts of a flow sensor.

6. The apparatus according to claim 3, wherein only one of said two pressure measuring channels is equipped with said capillary material.

7. The apparatus according to claim 6, wherein only one of said two pressure measuring channels equipped with said capillary material is the one first receiving the breathing gas exhaled by a patient.

8. The apparatus according to claim 3, wherein both said two pressure measuring channels are equipped with said capillary material.

9. The apparatus according to claim 1, further comprising a sampling tube guiding a sample of the breathing gas flowing along said flow channel to an analyzer for a gas analysis.

10. The apparatus according to claim 1, wherein said capillary material is made of cotton or a polymer.

11. The apparatus according to claim 1, wherein said capillary material is hydrophilic, but can also be hygroscopic material.

12. The apparatus according to claim 1, wherein said capillary material is a treatment of an inner wall of said pressure measuring channel inducing capillary suctioning of water.

13. The apparatus according to claim 1, wherein said capillary material is a porous surface of said pressure measuring channel with open cells.

14. The apparatus according to claim 1, wherein said capillary material is a surface of said pressure measuring channel with fine capillary grooves.

15. The apparatus according to claim 1, wherein said capillary material is configured to clear an obstruction of said pressure measuring channel created by the drop of water in (i) less than 1 minute, (ii) in less than 30 seconds, or (iii) in less than 10 seconds.

16. An apparatus for improving an accuracy of a pressure measurement made of a flowing breathing gas with drops of water or humidity, comprising:

a flow channel along which the breathing gas is flowing;

a restricting element in said flow channel for a differential pressure measurement; and at least two pressure measuring channels, one of said two pressure measuring channels being connected to one side of said restricting element and another of said two pressure measuring channels being connected to another side of said restricting element, said two pressure measuring channels transmitting pressure signals of the breathing gas on both sides of said restricting element to a measuring device to make said differential pressure measurement;

wherein at least one of said pressure measuring channels is equipped with a capillary material enabling capillary suctioning of water.

17. The apparatus according to claim 16, wherein said capillary material is made of cotton or a polymer.

18. The apparatus according to claim 16, wherein said capillary material is hydrophilic, but can also be hygroscopic material.

19. A flow sensor for a flow rate measurement of a breathing gas including drops of water or humidity, comprising:

a flow channel along which the breathing gas is flowing;

a restricting element in said flow channel for a differential pressure measurement; and at least two pressure measuring channels, one of said two pressure measuring channels being connected to one side of said restricting element and another of said two pressure measuring channels being connected to another side of said restricting element, said two pressure measuring channels transmitting pressure signals of the breathing gas on both sides of said restricting element to a measuring device to make the flow rate measurement;

wherein at least one of said pressure measuring channels is equipped with a capillary material enabling capillary suctioning of water for improving an accuracy of the flow rate measurement.

20. The flow sensor according to claim 19, further comprising a sampling tube guiding a sample of the breathing gas flowing along said flow channel to an analyzer for a gas analysis.

* * * * *